United States Patent
Zeun et al.

(10) Patent No.: US 9,885,678 B2
(45) Date of Patent: Feb. 6, 2018

(54) MEASURING SYSTEM FOR DETERMINING SPECIFIC ELECTRICAL CONDUCTIVITY

(71) Applicant: Endress + Hauser Conducta Gesellschaft für Mess- und Regeltechnik mbH + Co. KG, Maulburg (DE)

(72) Inventors: Hendrik Zeun, Chemnitz (DE); Stefan Paul, Dobeln (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 29 days.

(21) Appl. No.: 15/071,340

(22) Filed: Mar. 16, 2016

(65) Prior Publication Data
US 2016/0274045 A1 Sep. 22, 2016

(30) Foreign Application Priority Data

Mar. 20, 2015 (DE) .................. 10 2015 104 217

(51) Int. Cl.
| | |
|---|---|
| *G01R 27/08* | (2006.01) |
| *G01R 27/28* | (2006.01) |
| *G01N 27/02* | (2006.01) |
| *G01R 27/26* | (2006.01) |
| *G01N 27/06* | (2006.01) |

(52) U.S. Cl.
CPC .......... *G01N 27/025* (2013.01); *G01N 27/06* (2013.01); *G01R 27/267* (2013.01)

(58) Field of Classification Search
CPC ..... G01N 27/025; G01N 27/06; G01R 27/267
USPC .................. 324/691, 693, 696, 654
See application file for complete search history.

(56) References Cited

U.S. PATENT DOCUMENTS

| | | | |
|---|---|---|---|
| 4,816,758 A | 3/1989 | Theissen | |
| 5,089,781 A | 2/1992 | Arichika | |
| 5,189,366 A | 2/1993 | Mayo | |
| 9,410,910 B1 * | 8/2016 | Fougere | ................. G01N 27/06 |
| 2012/0326711 A1 * | 12/2012 | Roper | .................. G01N 27/025 324/252 |
| 2014/0260604 A1 * | 9/2014 | Ranwell | ............... G01N 27/048 73/335.01 |

FOREIGN PATENT DOCUMENTS

| | | |
|---|---|---|
| DE | 3439369 A1 | 4/1986 |
| DE | 68918825 T2 | 2/1995 |
| DE | 69119798 T2 | 12/1996 |

OTHER PUBLICATIONS

German Search Report, German PTO, Munich, dated Sep. 14, 2015.

\* cited by examiner

*Primary Examiner* — Amy He
(74) *Attorney, Agent, or Firm* — Mark A. Logan; PatServe

(57) ABSTRACT

A measuring system for determining the specific electrical conductivity of a medium in a vessel, comprising an inductive conductivity sensor with at least one transmitter coil that emits an input signal into the medium and a receiver coil connected to the transmitter coil via the medium that delivers the output signal, a temperature sensor for measuring the temperature of the medium, and a data processing unit that determines the conductivity of the medium using the input signal, the output signal, and the temperature provided. The system is characterized by the fact that the conductivity sensor and the temperature sensor are designed as non-invasive sensors.

9 Claims, 1 Drawing Sheet

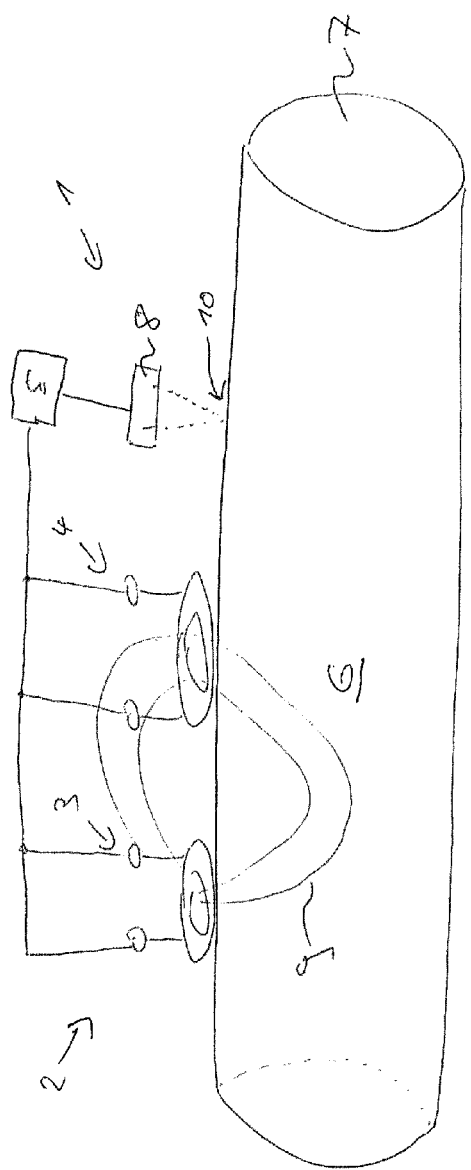
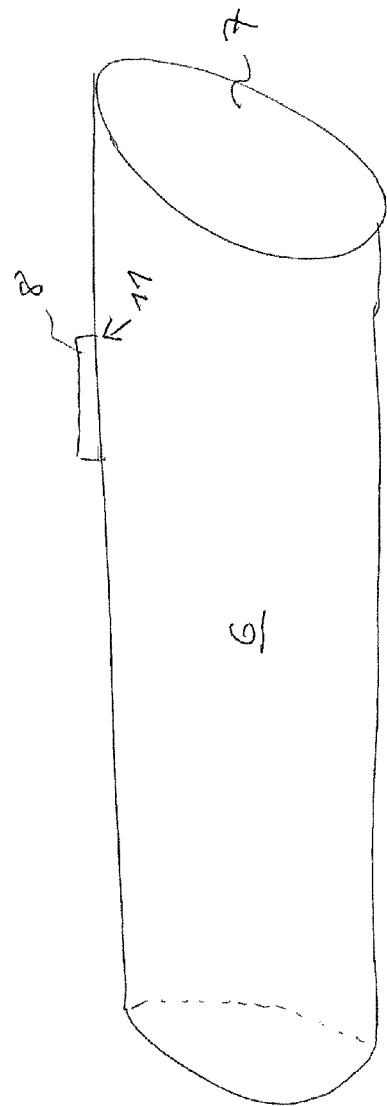

MEASURING SYSTEM FOR DETERMINING SPECIFIC ELECTRICAL CONDUCTIVITY

TECHNICAL FIELD

The invention pertains to a measuring system for determining the specific electrical conductivity of a medium in a vessel.

BACKGROUND DISCUSSION

In general, conductivity sensors that perform measurements according to an inductive or a conductive principle are used to measure the electrical conductivity of a medium in process automation.

For example, conductive conductivity sensors with at least two electrodes immersed in the medium to take measurements are known from the prior art. In order to determine the electrical conductivity of the medium, one determines the resistance or conductance of the electrode measuring path in the medium. If the cell constant is known, this information then serves to detect the conductivity of the medium. It is absolutely necessary that, in order to be able to measure the conductivity of a medium with a conductive conductivity sensor, at least two electrodes must come into contact with the measuring liquid.

The inductive principle of measuring the conductivity of process media assumes the use of sensors that are equipped with both a transmitter coil and a receiver coil installed at a distance from the transmitter coil. The transmitter coil produces an alternating electromagnetic field, which affects charged particles, e.g., ions, in the liquid medium and creates a corresponding electric current in the medium. As a result of this electric current, an electromagnetic field appears at the receiver coil, inducing a received signal (induction voltage) on the receiver coil according to Faraday's law of induction. This received signal can be analyzed and used to determine the electrical conductivity of the liquid medium.

Inductive conductivity sensors are typically constructed as follows: The transmitter coil and the receiver coil are, as a rule, built as toroidal coils, enveloping a continuous opening through which the medium can be applied, so that both the coils are encompassed in the medium. The excitation of the transmitter coil creates in the medium a closed current path that follows through both the transmitter coil and the receiver coil. By analyzing the current and voltage signals obtained at the receiver coil in response to the signal from the transmitter coil, the conductivity of the medium liquid can be determined. This principle is well established in industrial process measurement equipment, and has been documented in a large number of texts and patent literature—for example, in German Patent, DE 198 51 146 A1.

The Endress+Hauser group distributes such inductive conductivity sensors under such names as CLS50D, CLS54D, and CLD18.

In order to determine conductivity, it is necessary to know the temperature of the medium to be measured; as a rule, the conductivity increases with an increase in temperature. To measure temperature, a temperature sensor immersed in the medium, e.g., a Pt100, Pt1000, PTC, etc., is used. The temperature sensor is mostly situated in the casing, and comes into contact with the medium via an opening in the casing. Despite appropriate sealing measures, this opening creates a risk of leakage or leaks. This also means that more effort is required in implementing hygiene.

Even if the temperature sensor is not installed in the casing, it—like the part of a conductivity sensor that contacts the medium—must be connected via a flange leading to the vessel, in general, a process connection with a higher-level unit outside the medium. Here, as well, there is risk of leakage.

SUMMARY OF THE INVENTION

The invention is based upon the task of designing a measuring system that can overcome the disadvantages of present technology. It should be possible to attach the measuring system without any alterations to the vessel that contains the medium and minimize the risk of leakage.

This task is completed using a measuring system that comprises an inductive conductivity sensor with at least one transmitter coil that emits an input signal into the medium and a receiver coil connected to the transmitter coil via the medium that delivers the output signal, a temperature sensor for measuring the temperature of the medium, and a data processing unit that determines the conductivity of the medium using the input signal, the output signal, and the temperature of the medium provided. The system is characterized in that the conductivity sensor and the temperature sensor are designed as non-invasive sensors.

Thus, the measurement system measures the conductivity and the temperature without coming into contact with the medium, and then determines the temperature-corrected conductivity value. Neither the conductivity sensor, nor the temperature sensor are exposed to the temperature or the flow pressure of the medium. The measuring system can thus be built as a leak-proof measurement system.

The measurement system is mainly used in aqueous media, especially aqueous liquids, e.g. fresh water, wastewater, chemicals etc. The medium is located in a vessel, and can be either a flowing medium or stagnant water.

In an advantageous configuration, the conductivity sensor is a conductivity sensor working with the inductive principle. Hence, the medium to be measured flows at least through one coil of the inductive conductivity sensor. At least one coil is made as an ring or toroid coil where the water flows through or stands in.

In an advantageous configuration, the conductivity sensor is attached to an electrically non-conductive part of the vessel. Thus, the vessel itself can be made out of metal. If the conductivity sensor is attached to a non-conductive part of the vessel, the measurement will not be disturbed.

It is preferable that the conductivity sensor have a core with a relative permeability higher than 1—perhaps a ferrite or a mu-metal. This will lead to an amplification in the measurement signal.

In another advantageous further embodiment, the temperature sensor is designed as an optical sensor that has optical contact with the medium via a heat radiation-transparent area of the vessel.

This will lead to a faster response time in measuring temperature compared with the state-of-the-art technology. Owing to this, precise temperature-corrected conductivity measurement data are obtained more quickly.

In one variant, the temperature sensor is an infrared thermometer. The temperature can be measured very easily and quickly.

In an alternative embodiment, the temperature sensor measures the temperature on the surface of the vessel, and the data processing unit determines the temperature of the medium on the basis of this temperature.

It is preferable that the data processing unit determine the temperature on the basis of the temperature, of the vessel surface, its material, its wall thickness, and the ambient temperature.

In order to obtain a compact unit, the measuring system is designed as a single device, i.e., the conductivity sensor, the temperature sensor, and the data processing unit are located in the same casing.

BRIEF DESCRIPTION OF THE DRAWINGS

The invention is explained in more detail by means of the following figures. They show:

FIG. 1 is the measuring system according to the invention; and

FIG. 2 is a variant of the measuring system according to the invention.

In the figures, the same features are marked with the same reference symbols.

DETAILED DISCUSSION IN CONJUNCTION WITH THE DRAWINGS

The measuring system in its entirety is marked with the reference symbol 1 and is shown in FIG. 1. The measuring system (1) is designed for use in process automation.

The measuring system (1) is attached to the vessel (7), in which the medium to be measured (6) is located. The medium is an aqueous liquids, e.g. fresh water, wastewater, chemicals etc. The vessel (7) may be a pipe made, for example, out of plastic. Other materials, such as metal, are obviously possible for the vessel. However, the measuring system (1) must always be attached to an electrically non-conductive area of the vessel (7). If the vessel (7) is made out of metal, this could be an area made out of plastic. The medium in the vessel (7) can be either a flowing medium or stagnant water.

The measuring system (1) is equipped with a conductivity sensor (2). FIG. 1 shows this inductive conductivity sensor (2) with a transmitter coil (3) and a receiver coil (4). The transmitter coil (3) and the receiver coil (4) are located on opposite sides of a circuit board. In one variant, the coils (3, 4) are installed coaxially and sequentially as rotation symmetrical toroidal coils. In a second variant, the coils (3, 4) are installed on the circuit board as disk coils. The circuit board comprises the conductor paths (not shown here) that contact the coils, connecting the transmitter coil (3) with a driver circuit, and the receiver coil (4) with a receiver circuit. The driver circuit and the receiver circuit can form part of the sensor circuit installed on the circuit board.

The medium to be measured flows at least through one coil of the inductive conductivity sensor. At least one coil is made as an ring or toroid coil where the water flows through or stands in.

The conductivity sensor functions as a double transformer, in which the transmitter coil and the receiver coil (3, 4) are brought to the medium (6) in such a way that a closed current path (9) involving the transmitter and the receiver coils (3, 4) can be created in the medium (6). In order to amplify this current path (9) appropriately, the conductivity sensor (2) has a core with a relative permeability higher than 1, perhaps made out of ferrite or a mu-metal. When the transmitter coil (3) is excited with an alternating voltage signal used as an input signal, it creates a magnetic field in which a current path (9) involving the coils (3) and (4) is induced, the strength of the current depending upon the electric conductivity of the medium (6). Additionally, a current path is created in the medium (6) via ionic conduction. As this alternating current in the medium (6) creates a surrounding alternating magnetic field, an alternating current is induced in the receiver coil (4) as an output signal. This alternating current and, respectively, the alternating voltage delivered by the receiver coil (4) as its output signal, is the measure of the electric conductivity of the medium (6).

The measuring system (1) includes a temperature sensor (8) for measuring the temperature of the medium (6). Further included in the measuring system (1) is a data processing unit (5) which, on the basis of the input signal, the output signal, and the temperature of the medium (6), determines its conductivity.

The measuring system (1) can be designed as a single device.

The conductivity sensor (2) and the temperature sensor (8) are designed as non-invasive sensors. Thus, the conductivity sensor (2) and the temperature sensor (8) do not come into contact with the medium (6). The sensors (2, 8) are attached outside the vessel (7).

The temperature sensor (8) is designed as an optical sensor (see FIG. 1). The sensor (8) has optical contact with the medium (6) via a heat radiation-transparent area (10) of the vessel (7). In one variant, the temperature sensor (8) is an infrared thermometer.

Alternatively, as shown in FIG. 2, the temperature sensor (8) measures the temperature at the surface (11) of the vessel (7). The conductivity sensor 2 is no longer shown in FIG. 2. In this case, the temperature sensor (8) can be a contactless optical sensor or a contact sensor. The data processing unit (5) determines the temperature of the medium (6). In order to complete this task, the data processing unit (5) additionally needs the material of the vessel (7)—particularly, its heat conductivity—the wall thickness of the vessel (7), the ambient temperature—i.e., the temperature outside the vessel (7)—as well as the distance of the sensor from the vessel when measuring the ambient temperature. Additional temperature sensors can be used to determine the ambient temperature. These additional temperature sensors should be arranged outside the vessel in appropriate positions. The appropriate positioning and the optimum number of additional temperature sensors make it possible to determine the temperature gradients present and, thus, the temperature of the medium.

The invention claimed is:

1. A measuring system for determining a specific electrical conductivity of a medium in a vessel, comprising:
   an inductive conductivity sensor, comprising:
      a transmitter coil embodied to emit a first electromagnetic signal into the medium based on an electrical input signal to the transmitter coil,
      a receiver coil embodied to receive a second electromagnetic signal from the medium, the receiver coil further embodied to generate an electrical output signal based on the second electromagnetic signal;
   a temperature sensor embodied to measure a temperature of the medium; and
   a data processing unit electrically connected to the transmitter coil, the receiver coil, and the temperature sensor, the data processing unit embodied to generate the electrical input signal to the transmitter coil and to receive the electrical output signal from the receiver coil, the data processing unit configured to determine the conductivity of the medium on the basis of the input signal, the output signal, and the temperature of the medium, wherein the transmitter coil and the receiver coil are disposed on an electrically non-conducting outside surface of the vessel, and the temperature sensor is disposed on a second outside surface of the vessel.

2. The measuring system according to claim 1, in which said conductivity sensor has a core with a relative permeability higher than 1.

3. The measuring system according to claim 1, in which said temperature sensor has optical contact with the medium via a heat radiation-transparent area of said vessel.

4. The measuring system according to claim 3, in which said temperature sensor is an infrared thermometer.

5. The measuring system according to claim 1, wherein said temperature sensor is embodied to measure a temperature of the second outside surface of the vessel, and the data processing unit is further configured to determine the temperature of the medium on the basis of the temperature of the second outside surface of the vessel.

6. The measuring system according to claim 5, in which said data processing unit is further configured to determine the temperature of the medium on the basis of the temperature of the second outside surface of the vessel, a material of a vessel wall, a thickness of the vessel wall, and an ambient temperature.

7. The measuring system according to claim 1, in which the measuring system is designed as a single device.

8. The measuring system of claim 1, wherein the transmitter coil is disposed on the electrically non-conducting outside surface and the receiver coil is disposed on the electrically non-conducting outside surface at a pre-determined radial distance from the transmitter coil such that the receiver coil and the transmitter coil do not overlap.

9. The measuring system of claim 1, wherein the transmitter coil is disposed on the electrically non-conducting outside surface co-axially with the receiver coil.

* * * * *